US010179815B2

(12) United States Patent
Soukupova et al.

(10) Patent No.: US 10,179,815 B2
(45) Date of Patent: Jan. 15, 2019

(54) ANTIBODIES SPECIFICALLY BINDING TO HER3

(71) Applicants: Roche Molecular Systems, Inc., Pleasanton, CA (US); Ventana Medical Systems, Inc., Tucson, AZ (US)

(72) Inventors: Monika Soukupova, Wessobrunn (DE); Michael Schraeml, Penzberg (DE); Birgit Bossenmaier, Seefeld (DE); Patrick C. Roche, Tucson, AZ (US); Michael Gerg, Munich (DE); Sebastian Dziadek, Benediktbeuern (DE)

(73) Assignees: VENTANA MEDICAL SYSTEMS, INC., Tucson, AZ (US); ROCHE MOLECULAR SYSTEMS, INC., Pleasanton, CA (US)

( * ) Notice: Subject to any disclaimer, the term of this patent is extended or adjusted under 35 U.S.C. 154(b) by 0 days.

(21) Appl. No.: 15/083,686

(22) Filed: Mar. 29, 2016

(65) Prior Publication Data

US 2017/0096487 A1    Apr. 6, 2017

Related U.S. Application Data

(63) Continuation of application No. PCT/EP2014/071204, filed on Oct. 2, 2014.

(30) Foreign Application Priority Data

Oct. 4, 2013  (EP) .................................... 13004801
Oct. 18, 2013 (EP) .................................... 13005008

(51) Int. Cl.
*C07K 16/28* (2006.01)
*C07K 16/32* (2006.01)
*C07K 16/30* (2006.01)
*G01N 1/30* (2006.01)
*G01N 33/574* (2006.01)
*G01N 33/74* (2006.01)

(52) U.S. Cl.
CPC ...... *C07K 16/2863* (2013.01); *C07K 16/3023* (2013.01); *C07K 16/3046* (2013.01); *C07K 16/32* (2013.01); *G01N 1/30* (2013.01); *G01N 33/57492* (2013.01); *G01N 33/74* (2013.01); *C07K 2317/33* (2013.01); *C07K 2317/56* (2013.01); *C07K 2317/565* (2013.01); *C07K 2317/92* (2013.01); *C07K 2317/94* (2013.01); *G01N 2001/302* (2013.01); *G01N 2333/71* (2013.01)

(58) Field of Classification Search
None
See application file for complete search history.

(56) References Cited

U.S. PATENT DOCUMENTS

| 4,179,337 A | 12/1979 | Davis et al. |
| 4,301,144 A | 11/1981 | Lwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 2011/0033482 A1 | 2/2011 | Ullrich et al. |

FOREIGN PATENT DOCUMENTS

| EP | 2138511 A1 | 12/2009 |
| JP | 2012515226 A | 7/2012 |
| JP | 2013544492 A | 12/2013 |
| WO | 2010/083470 A1 | 7/2010 |
| WO | 2012/031198 A2 | 3/2012 |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
Alimandi, Maurizio et al., Cooperative signaling of ErbB3 and ErbB2 in neoplastic transformation and human mammary carcinomas, Oncogene, 1995, pp. 1813-1821, vol. 10.
Barnes, Louise M. et al., Advances in animal cell recombinant protein production: GTS-NS0 expression system, Cytotechnology, 2000, pp. 109-123, vol. 32.
Barnes, Louise M. et al., Characterization of the Stability of Recombinant Protein Production in the GS-NS0 Expression System, Biotechnology and Bioengineering, 2001, pp. 261-270, vol. 73.
Brown, McKay et al., Tolerance to Single, but Not Multiple, Amino Acid Replacements in Antibody VH CDR2 A Means of Minimizing B Cell Wastage from Somatic Hypermutation?, The Journal of Immunology, 1996, pp. 3285-3291, vol. 156.
Carter, Paul et al., Humanization of an anti-p185HER2 antibody for human cancer therapy, Proceedings of the National Academy of Sciences USA, 1992, pp. 4285-4289, vol. 89.
Durocher, Yves et al., High-level and high-throughput recombinant protein production by transient transfection of suspension-growing human 293-EBNA1 cells, Nucleic Acids Research, 2002, 9 pps., vol. 30, No. 2, e9.
Engvall, Eva, [28] Enzyme Immunoassay ELISA and EMIT, Methods in Enzymology, 1980, pp. 419-439, vol. 70.
Geisse, S. et al, Eukaryotic Expression Systems: A Comparison, Protein Expression and Purification, 1996, 271-282, 8.

(Continued)

*Primary Examiner* — Nelson B Moseley, II
(74) *Attorney, Agent, or Firm* — Ventana Medical Systems, Inc.

(57) ABSTRACT

The present invention relates to isolated antibodies, or an antigen portions thereof, which bind to human HER3. The novel antibodies are of great utility since they allow for the sensitive and specific detection of human HER3. Detection of human HER3 is, e.g., possible in a tissue sample, even when such tissue sample is a formalin-fixed paraffin embedded tissue (FFPET) sample.

20 Claims, 8 Drawing Sheets

Specification includes a Sequence Listing.

(56) References Cited

OTHER PUBLICATIONS

Hellyer, Nathan J. et al., Heregulin-dependent Activation of Phosphoinositide 3-Kinase and Akt via the ErbB2/ErbB3, Co-receptor, The Journal of Biological Chemistry, 2001, pp. 42153-42161, vol. 276, No. 45.
International Search Report dated Jan. 8, 2015 in Application No. PCT/EP2014/071204, 5 pages.
Kufman, Randal J., Overview of Vector Design for Mammalian Gene Expression, Molecular Biotechnology, 2000, pp. 151-161, vol. 16.
Kraus, Matthias et al., Demonstration of ligand-dependent signaling by the erbB-3 tyrosine kinase and its constitutive activation in human breast tumor cells, Proceedings of the National Academy of Sciences USA, 1993, pp. 2900-2904, vol. 90.
Kraus, Matthias H. et al., Isolation and characterization of ERBB3, a third member of the ERBB/epidermal growth factor receptor family: Evidence for overexpression in a subset of human mammary tumors, Proceedings of the National Academy of Sciences USA, 1989, pp. 9193-9197, vol. 86.
Köhler, G. and Milstein, C., Continuous cultures of fused cells secreting antibody of predefined specificity, Nature, 1975, pp. 495-497, vol. 256.
Makrides, Savvas C., Components of Vectors for Gene Transfer and Expression in Mammalian Cells, Protein Expression and Purification, 1999, pp. 183-202, vol. 17.
Norderhaug, Lars et al., Versatile vectors for transient and stable expression of recombinant antibody molecules in mammalian cells, Journal of Immunological Methods, 1997, pp. 77-87, vol. 204.
Orlandi, Rosaria et al., Cloning immunoglobulin variable domains for experssion by the polymerase chain reaction, Proceedings of the National Academy of Sciences USA, 1989, pp. 3833-3837, vol. 86.
Plowman, Gregory D. et al., Molecular cloning and expression of an additional epidermal growth factor receptor-related gene, Proceedings of the National Academy of Sciences USA, 1990, pp. 4905-4909, vol. 87.
Queen, Cary et al., A humanized antibody that binds to the interleukin 2 receptor, Proceedings of the National Academy of Sciences USA, 1989, pp. 10029-10033, vol. 86.
Riechmann, Lutz et al., Reshaping human antibodies for therapy, Nature, 1988, pp. 323-327, vol. 332.
Schaefer, Karl-Ludwig et al., Constitutive Activation of Neuregulin/ERBB3 Signaling Pathway in Clear Cell Sarcoma of Soft Tissue, Neoplasia, 2006, pp. 613-622, vol. 8, No. 7.
Schlaeger, Ernst-Jürgen and Christensen, Klaus, Transient gene expression in mammalian cells grown in serum-free suspension culture, Cytotechnology, 1999, pp. 71-83, vol. 30.
Schlaeger, Ernst-Jürgen, The protein hydrolysate, Primatone RL, is a cost-effective multiple growth promoter of mammalian cell culture in serum-containing and serum-free media and displays anti-apoptosis properties, Journal of Immunological Methods, 1996, pp. 191-199, vol. 194.
Singer, Elizabeth et al., Identification of a Heregulin Binding Site in HER3 Extracellular Domain, The Journal of Biological Chemistry, 2001, pp. 44266-44274, vol. 276, No. 47.
Sliwkowski, Mark S. et al., Coexpression of erbB2 and erbB3 Proteins Reconstitutes a High Affinity Receptor for Heregulin, The Journal of Biological Chemistry, 1994, pp. 14661-14665, vol. 269, No. 20.
UniProtKB-Q9NZQ7 (PD1L1_HUMAN, 6 pages.
Werner, Rolf G. et al., Appropriate Mammalian Expression Systems for Biopharmaceuticals, Drug Research, 1998, pp. 870-880, vol. 48 (II), No. 8.

* cited by examiner

SEQUENCE LISTING

<160> NUMBER OF SEQ ID NOS: 13

<210> SEQ ID NO 1
<211> LENGTH: 8
<212> TYPE: PRT
<213> ORGANISM: Artificial Sequence
<220> FEATURE:
<223> OTHER INFORMATION: Sequence of CDR1H

```
<400> SEQUENCE: 1

Thr Phe Thr Asp Tyr Asn Leu His
1               5

<210> SEQ ID NO 2
<211> LENGTH: 14
<212> TYPE: PRT
<213> ORGANISM: Artificial Sequence
<220> FEATURE:
<223> OTHER INFORMATION: Sequence of CDR2H, variant 1

<400> SEQUENCE: 2

Tyr Phe Asn Pro Tyr Asn Gly Gly Thr Phe Tyr Thr Gln Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Sequence of CDR2H, variant 2

<400> SEQUENCE: 3

Tyr Phe Asn Thr Tyr Asn Gly Gly Ile Phe Tyr Thr Gln Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Sequence of CDR3H

<400> SEQUENCE: 4

Thr Arg Arg Tyr Phe Asp Gly Ser Ser Tyr Phe
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Sequence of CDR1L

<400> SEQUENCE: 5

Arg Ser Ser Gln Thr Ile Val His
1               5

<210> SEQ ID NO 6
<211> LENGTH: 5
<212> TYPE: PRT
<213> ORGANISM: Artificial Sequence
<220> FEATURE:
<223> OTHER INFORMATION: Sequence of CDR2L, variant 1

<400> SEQUENCE: 6

Gln Ser Leu Lys Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Sequence of CDR2L, variant 2

<400> SEQUENCE: 7
```

```
Gln Ser Pro Lys Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Sequence of CDR3L

<400> SEQUENCE: 8

Phe Gln Gly Ser His Val Pro Arg Ala
1               5

<210> SEQ ID NO 9
<211> LENGTH: 120
<212> TYPE: PRT
<213> ORGANISM: Artificial Sequence
<220> FEATURE:
<223> OTHER INFORMATION: Sequence of VH, variant 1:

<400> SEQUENCE: 9

Glu Val Gln Leu Leu Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Asn Leu His Trp Val Lys Gln Ser His Gly Arg Thr Leu Glu Trp Ile
            35                  40                  45

Gly Tyr Phe Asn Pro Tyr Asn Gly Gly Thr Tyr Thr Gln Lys Phe
        50                  55                  60

Lys Asp Lys Ala Thr Leu Thr Ile Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Arg Tyr Phe Asp Gly Ser Ser Tyr Phe Asp Tyr Trp Gly Gln
                100                 105                 110

Gly Thr Thr Leu Thr Val Ser Ser
            115                 120

<210> SEQ ID NO 10
<211> LENGTH: 120
<212> TYPE: PRT
<213> ORGANISM: Artificial Sequence
<220> FEATURE:
<223> OTHER INFORMATION: Sequence of VH, variant 2

<400> SEQUENCE: 10

Glu Val Gln Leu Gln Gln Ser Gly Pro Glu Leu Ala Lys Pro Gly Ala
1               5                   10                  15

Ser Val Lys Met Ser Cys Lys Ala Ser Gly Tyr Thr Phe Thr Asp Tyr
                20                  25                  30

Asn Leu His Trp Val Lys Gln Ser His Gly Lys Thr Leu Glu Trp Ile
            35                  40                  45

Gly Tyr Phe Asn Thr Tyr Asn Gly Gly Ile Tyr Thr Gln Lys Phe
        50                  55                  60

Lys Asp Lys Ala Thr Leu Thr Ile Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95
```

Thr Arg Arg Tyr Phe Asp Gly Ser Ser Tyr Phe Asp Tyr Trp Gly Arg
            100                 105                 110

Gly Thr Thr Leu Thr Val Ser Ser
        115                 120

<210> SEQ ID NO 11
<211> LENGTH: 113
<212> TYPE: PRT
<213> ORGANISM: Artificial Sequence
<220> FEATURE:
<223> OTHER INFORMATION: Sequence of VL, variant 1

<400> SEQUENCE: 11

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Val Gln Lys Pro Gly Gln Ser
        35                  40                  45

Leu Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Arg Ala Phe Gly Gly Gly Thr Lys Leu Glu Ile Lys
            100                 105                 110

Arg

<210> SEQ ID NO 12
<211> LENGTH: 113
<212> TYPE: PRT
<213> ORGANISM: Artificial Sequence
<220> FEATURE:
<223> OTHER INFORMATION: Sequence of VL, variant 2

<400> SEQUENCE: 12

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Val Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ala Pro Arg Thr Phe Gly Gly Gly Thr Lys Leu Glu Ile Lys
            100                 105                 110

Arg

<210> SEQ ID NO 13
<211> LENGTH: 1342
<212> TYPE: PRT
<213> ORGANISM: Homo sapiens

<400> SEQUENCE: 13

```
Met Arg Ala Asn Asp Ala Leu Gln Val Leu Gly Leu Phe Ser Leu
1               5                   10                  15

Ala Arg Gly Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
        50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415
```

```
Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Asp Cys Val Ala Glu
            485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
            530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
            645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
            725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
            755                 760                 765

Ala His Ile Val Arg Leu Leu Gly Leu Cys Pro Gly Ser Ser Leu Gln
            770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
            805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
```

```
                835                 840                 845
Gln Val Ala Asp Phe Gly Val Ala Asp Leu Leu Pro Pro Asp Asp Lys
    850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                885                 890                 895
Tyr Gly Val Thr Val Trp Glu Leu Met Thr Phe Gly Ala Glu Pro Tyr
            900                 905                 910
Ala Gly Leu Arg Leu Ala Glu Val Pro Asp Leu Leu Glu Lys Gly Glu
        915                 920                 925
Arg Leu Ala Gln Pro Gln Ile Cys Thr Ile Asp Val Tyr Met Val Met
    930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                965                 970                 975
Val Ile Lys Arg Glu Ser Gly Pro Gly Ile Ala Pro Gly Pro Glu Pro
            980                 985                 990
His Gly Leu Thr Asn Lys Lys Leu Glu Glu Val Glu Leu Glu Pro Glu
        995                 1000                1005
Leu Asp Leu Asp Leu Asp Leu Glu Ala Glu Glu Asp Asn Leu Ala
    1010                1015                1020
Thr Thr Thr Leu Gly Ser Ala Leu Ser Leu Pro Val Gly Thr Leu
    1025                1030                1035
Asn Arg Pro Arg Gly Ser Gln Ser Leu Leu Ser Pro Ser Ser Gly
    1040                1045                1050
Tyr Met Pro Met Asn Gln Gly Asn Leu Gly Glu Ser Cys Gln Glu
    1055                1060                1065
Ser Ala Val Ser Gly Ser Ser Glu Arg Cys Pro Arg Pro Val Ser
    1070                1075                1080
Leu His Pro Met Pro Arg Gly Cys Leu Ala Ser Glu Ser Ser Glu
    1085                1090                1095
Gly His Val Thr Gly Ser Glu Ala Glu Leu Gln Glu Lys Val Ser
    1100                1105                1110
Met Cys Arg Ser Arg Ser Arg Ser Arg Ser Pro Arg Pro Arg Gly
    1115                1120                1125
Asp Ser Ala Tyr His Ser Gln Arg His Ser Leu Leu Thr Pro Val
    1130                1135                1140
Thr Pro Leu Ser Pro Pro Gly Leu Glu Glu Glu Asp Val Asn Gly
    1145                1150                1155
Tyr Val Met Pro Asp Thr His Leu Lys Gly Thr Pro Ser Ser Arg
    1160                1165                1170
Glu Gly Thr Leu Ser Ser Val Gly Leu Ser Ser Val Leu Gly Thr
    1175                1180                1185
Glu Glu Glu Asp Glu Asp Glu Glu Tyr Glu Tyr Met Asn Arg Arg
    1190                1195                1200
Arg Arg His Ser Pro Pro His Pro Pro Arg Pro Ser Ser Leu Glu
    1205                1210                1215
Glu Leu Gly Tyr Glu Tyr Met Asp Val Gly Ser Asp Leu Ser Ala
    1220                1225                1230
Ser Leu Gly Ser Thr Gln Ser Cys Pro Leu His Pro Val Pro Ile
    1235                1240                1245
```

```
Met Pro Thr Ala Gly Thr Thr Pro Asp Glu Asp Tyr Glu Tyr Met
    1250            1255            1260

Asn Arg Gln Arg Asp Gly Gly Gly Pro Gly Gly Asp Tyr Ala Ala
    1265            1270            1275

Met Gly Ala Cys Pro Ala Ser Glu Gln Gly Tyr Glu Glu Met Arg
    1280            1285            1290

Ala Phe Gln Gly Pro Gly His Gln Ala Pro His Val His Tyr Ala
    1295            1300            1305

Arg Leu Lys Thr Leu Arg Ser Leu Glu Ala Thr Asp Ser Ala Phe
    1310            1315            1320

Asp Asn Pro Asp Tyr Trp His Ser Arg Leu Phe Pro Lys Ala Asn
    1325            1330            1335

Ala Gln Arg Thr
    1340
```

ANTIBODIES SPECIFICALLY BINDING TO HER3

CROSS-REFERENCE TO RELATED APPLICATIONS

This application is a continuation of International Application No. PCT/EP2014/071204 filed Oct. 2, 2014, which claims priority to EP Patent Application No. 13004801.0 filed Oct. 4, 2013, and EP Patent Application No. 13005008.1 filed Oct. 18, 2013, the disclosures of which are hereby incorporated by reference in their entirety.

BACKGROUND OF THE INVENTION

The present invention relates to isolated antibodies specifically binding to human HER3, methods for performing immunohistochemistry using these antibodies, and methods for their production.

Human HER3 (ErbB-3, ERBB3, c-erbB-3, c-erbB3, receptor tyrosine-protein kinase erbB-3, SEQ ID NO: 17) encodes a member of the epidermal growth factor receptor (EGFR) family of receptor tyrosine kinases which also includes HER1 (also known as EGFR), HER2, and HER4 (Kraus, M. H. et al., PNAS 86 (1989) 9193-9197; Plowman, G. D. et al., PNAS 87 (1990) 4905-4909; Kraus, M. H. et al., PNAS 90 (1993) 2900-2904). Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase domain (TKD) and a C-terminal phosphorylation domain. This trans-membrane protein has a Heregulin (HRG) binding domain within the extracellular domain but not an active kinase domain. It therefore can bind this ligand but not convey the signal into the cell through protein phosphorylation. However, it does form heterodimers with other HER family members which do have kinase activity. Heterodimerization leads to the activation of the receptor-mediated signaling pathway and transphosphorylation of its intracellular domain. Dimer formation between HER family members expands the signaling potential of HER3 and is a means not only for signal diversification but also signal amplification. For example the HER2/HER3 heterodimer induces one of the most important mitogenic signals via the PI3K and AKT pathway among HER family members (Sliwkowski M. X., et al., J. Biol. Chem. 269 (1994) 14661-14665; Alimandi M, et al., Oncogene. 10 (1995) 1813-1821; Hellyer, N. J., J. Biol. Chem. 276 (2001) 42153-4261; Singer, E., J. Biol. Chem. 276 (2001) 44266-44274; Schaefer, K. L., Neoplasia 8 (2006) 613-622).

Amplification of this gene and/or overexpression of its protein have been reported in numerous cancers, including prostate, bladder, and breast tumors. Alternate transcriptional splice variants encoding different isoforms have been characterized.

One isoform lacks the intermembrane region and is secreted outside the cell. This form acts to modulate the activity of the membrane-bound form. Additional splice variants have also been reported, but they have not been thoroughly characterized.

Despite the fact that human HER3 is known since more than twenty years it has been and even today is extremely difficult to detect the protein HER3 in a tissue sample. However, detecting HER3 in a tissues sample is crucial to correlate structure and morphology of a given sample with the localization, tissue distribution and/or concentration of HER3 to a biological function, in particular to a pathophysiological context related to numerous cancers.

While several anti-HER3 antibodies are available as research reagents from various companies, no satisfactory staining of a tissue sample, especially of a tissue sample that has been formalin-fixed and paraffin-embedded would appear to be possible using those reagents. In particular there is a need for antibodies showing a high binding specificity and sensitivity towards HER3 when used in automated staining systems for tissue samples such as Ventana Benchmark XT.

It was the task of the present invention to identify an antibody that specifically binds to the human HER3 protein and that can at least partially overcome the problems known in the art.

SUMMARY OF THE INVENTION

The present invention relates to an isolated antibody, or an antigen binding portion thereof, binding to human HER3, where the antibody comprises a heavy chain variable domain comprising a CDR1H region comprising the amino acid sequence of SEQ ID NO: 1, a CDR2H region comprising the amino acid sequence of SEQ ID NO: 2 or SEQ ID NO: 3, and a CDR3H region comprising the amino acid sequence of SEQ ID NO: 4, and a light chain variable domain comprising a CDR1L region comprising the amino acid sequence of SEQ ID NO: 5, a CDR2L region comprising the amino acid sequence of SEQ ID NO: 6 or SEQ ID NO: 7, and a CDR3L region comprising the amino acid sequence of SEQ ID NO: 8.

The present invention further comprises an isolated antibody, or an antigen binding portion thereof, binding to human HER3, and having a heavy chain variable domain comprising the amino acid sequence of SEQ ID NO: 9 or SEQ ID NO: 10, and a light chain variable domain comprising the amino acid sequence of SEQ ID NO: 11 or SEQ ID NO: 12.

The present invention also comprises an isolated antibody, or an antigen binding portion thereof, binding to human HER3 and having a heavy chain variable domain comprising a CDR1H region comprising an amino acid sequence modified from SEQ ID NO: 1 by one or more conservative amino acid substitutions, a CDR2H region comprising an amino acid sequence modified from SEQ ID NO: 2 or modified from SEQ ID NO: 3 by one or more conservative amino acid substitutions, and a CDR3H region comprising an amino acid sequence modified from SEQ ID NO: 4 by one or more conservative amino acid substitutions, and a light chain variable domain comprising a CDR1L region comprising an amino acid sequence modified from SEQ ID NO: 5 by one or more conservative amino acid substitutions, a CDR2L region comprising an amino acid sequence modified from SEQ ID NO: 6 or modified from SEQ ID NO: 7 by one or more conservative amino acid substitutions, and a CDR3L region comprising an amino acid sequence modified from SEQ ID NO: 8 by one or more conservative amino acid substitutions. In one embodiment of the present invention, the CDR1L region comprises an amino acid sequence modified from SEQ ID NO: 5 by a conservative amino acid substitution at position 5. In a further embodiment, the conservative amino acid substitution at position 5 of SEQ ID NO: 5 is a threonine/serin substitution. In another embodiment of the present invention, the CDR3L region comprises an amino acid sequence modified from SEQ ID NO: 8 by a conservative amino acid substitution at position 6 or position 9, or the CDR3L region comprises an amino acid sequence modified from SEQ ID NO: 8 by a conservative amino acid substitution at position 6 and position 9. In a further embodiment, the conservative amino acid substitution at position 6 of SEQ ID NO: 8 is a valin/alanin substitution or the conservative amino acid substitution at position 9 of SEQ ID NO: 8 is an alanin/threonin substitution. In another embodiment, the CDR3L region comprises an amino acid sequence modified from SEQ ID NO: 8 by a conservative amino acid substitution at position 6 and position 9, wherein the conservative amino acid substitution at position 6 of SEQ ID NO: 8 is a valin/alanin substitution and the conservative amino acid substitution at position 9 of SEQ ID NO: 8 is an alanin/threonin substitution.

Another aspect of the present invention provides for an isolated antibody, or an antigen binding portion thereof, which binds to human HER3, where the antibody comprises a heavy chain variable domain comprising an amino acid sequence with at least 95% sequence identity to SEQ ID NO: 9 or SEQ ID NO: 10, and a light chain variable domain with at least 95% sequence identity to SEQ ID NO: 11 or SEQ ID NO: 12.

In one embodiment the antibody of the present invention is a monoclonal antibody.

In another embodiment the antibody of the present invention is an antibody of the IgG subclass.

It has surprisingly been found that any of the aforementioned antibodies of the present invention have quite advantageous properties and can overcome at least some of the problems known in the art. They can be used with great advantage in an immunohistological staining procedure to detect the human HER3 protein. It is especially surprising and worth mentioning that the antibodies according to the present invention yield excellent staining results even with a formalin-fixed paraffin-embedded tissue (FFPET) sample. As such, the antibodies according to the present invention are particularly useful for the detection of human HER3 in FFPET samples processed in automated staining procedures.

Accordingly, the present invention also relates to a method for performing immunohistochemistry, the method comprising the steps of incubating a tissue sample with an antibody according to the present invention, whereby binding of said antibody to human HER3 in said tissue takes place and staining said tissue sample for the anti-HER3 antibody bound to the tissue sample.

In one embodiment the present invention relates to the use of an antibody according to the present invention in the immunohistochemical detection of human HER3, especially in a formaldehyde-fixed paraffin-embedded tissue (FFPET) sample.

Another embodiment of the present invention relates to kits useful for facilitating the practice of an immunohistochemical detection of human HER3. In one embodiment, a kit is provided for the detection of human HER3 in a formaldehyde-fixed paraffin-embedded tissue (FFPET) sample, said kit comprising an antibody, or an antigen binding portion thereof, according to the invention, and reagents for the detection of said antibody, or an antigen binding portion thereof.

Another aspect of the present invention provides for a nucleic acid encoding a heavy and a light chain of an anti-HER3 antibody provided herein.

In one embodiment the nucleic acid encodes the heavy and light chain of an anti-HER3 antibody, wherein the heavy chain variable domain comprises a CDR1H region comprising the amino acid sequence of SEQ ID NO: 1, a CDR2H region comprising the amino acid sequence of SEQ ID NO: 2 or SEQ ID NO: 3, and a CDR3H region comprising the amino acid sequence of SEQ ID NO: 4, and the light chain variable domain comprises a CDR1L region comprising the amino acid sequence of SEQ ID NO: 5, a CDR2L region comprising the amino acid sequence of SEQ ID NO: 6 or SEQ ID NO: 7, and a CDR3L region comprising the amino acid sequence of SEQ ID NO: 8.

In another embodiment the nucleic acid encodes the heavy and light chain of an anti-HER3 antibody, wherein the heavy chain variable domain comprises a CDR1H region comprising an amino acid sequence modified from SEQ ID NO: 1 by one or more conservative amino acid substitutions, a CDR2H region comprising an amino acid sequence modified from SEQ ID NO: 2 or SEQ ID NO: 3 by one or more conservative amino acid substitutions, and a CDR3H region comprising an amino acid sequence modified from SEQ ID NO: 4 by one or more conservative amino acid substitutions, and the light chain variable domain comprises a CDR1L region comprising an amino acid sequence modified from SEQ ID NO: 5 by one or more conservative amino acid substitutions, a CDR2L region comprising an amino acid sequence modified from SEQ ID NO: 6 or SEQ ID NO: 7 by one or more conservative amino acid substitutions, and a CDR3L region or comprising an amino acid sequence modified from SEQ ID NO: 8 by one or more conservative amino acid substitutions.

In a further embodiment the nucleic acid encodes the heavy and light chain of an anti-HER3 antibody, wherein the heavy chain variable domain comprises the amino acid sequence of SEQ ID NO: 9 or SEQ ID NO: 10, and the light chain variable domain comprises the amino acid sequence of SEQ ID NO: 11 or SEQ ID NO: 12.

In another embodiment the nucleic acid encodes the heavy and light chain of an anti-HER3 antibody, wherein the heavy chain variable domain comprises an amino acid sequence with at least 95% sequence identity to SEQ ID NO: 9 or SEQ ID NO: 10, and the light chain variable domain comprises an amino acid sequence with at least 95% sequence identity to SEQ ID NO: 11 or SEQ ID NO: 12.

The invention further comprises an expression vector comprising a nucleic acid according to the invention for the expression of an antibody according to the invention in a prokaryotic or eukaryotic host cell.

The invention further comprises a prokaryotic or eukaryotic host cell comprising a vector according to the invention.

The invention further comprises a method for the production of a recombinant antibody according to the invention, characterized by expressing a nucleic acid according to the invention in a prokaryotic or eukaryotic host cell and recovering said antibody from said cell or the cell culture supernatant.

Description of the Sequence Listing

| Sequence | | HER3 monoclonal antibody MAK < human HER3 > clone |
|---|---|---|
| SEQ ID NO: 1 | Sequence of CDR1H: TFTDYNLH | M- 7.2.42<br>M- 7.3.8 |
| SEQ ID NO: 2 | Sequence of CDR2H, variant 1: YFNPYNGGTFYTQK | M- 7.2.42 |
| SEQ ID NO: 3 | Sequence of CDR2H, variant 2: YFNTYNGGIFYTQK | M- 7.3.8 |

-continued

| Sequence | HER3 monoclonal antibody MAK < human HER3 > clone |
|---|---|
| SEQ ID NO: 4 Sequence of CDR3H: TRRYFDGSSYF | M- 7.2.42<br>M- 7.3.8 |
| SEQ ID NO: 5 Sequence of CDR1L: RSSQTIVH | M- 7.2.42 |
| SEQ ID NO: 6 Sequence of CDR2L, variant 1: QSLKL | M- 7.2.42 |
| SEQ ID NO: 7 Sequence of CDR2L, variant 2: QSPKL | M- 7.3.8 |
| SED ID NO: 8 Sequence of CDR3L: FQGSHVPRA | M- 7.2.42 |
| SEQ ID NO: 9 Sequence of VH, variant 1: EVQLLQSGPELVKPGASV KMSCKASGYTFTDYNLHW VKQSHGRTLEWIGYFNPY NGGTFYTQKFKDKATLTI NKSSSTAYMELRSLTSED SAVYYCTRRYFDGSSYFD YWGQGTTLTVSS | M- 7.2.42 |
| SEQ ID NO: 10 Sequence of VH, variant 2: EVQLQQSGPELAKPGASV KMSCKASGYTFTDYNLHW VKQSHGKTLEWIGYFNTY NGGIFYTQKFKDKATLTI NKSSSTAYMELRSLTSED SAVYYCTRRYFDGSSYFD YWGRGTTLTVSS | M- 7.3.8 |
| SEQ ID NO: 11 Sequence of VL, variant 1: DVLMTQTPLSLPVSLGDQ ASISCRSSQTIVHSNGNT YLEWYVQKPGQSLKLLIY KVSNRFSGVPDRFSGSGS GTDFTLKISRVEAEDLGV YYCFQGSHVPRAFGGGTK LEIKR | M- 7.2.42 |
| SEQ ID NO: 12 Sequence of VL, variant 2: DVLMTQIPLSLPVSLGDQ ASISCRSSQSIVHSNGNT YLEWYVQKPGQSPKLLIY KVSNRFSGVPDRFSGSGS GTDFTLKISRVEAEDLGV YYCFQGSHAPRTFGGGTK LEIKR | M- 7.3.8 |

Formalin fixed paraffin embedded HEK293 cells overexpressing HER1, HER2, HER3 or HER4 were analyzed on the Ventana automated slide stainer Benchmark XT instrument, using the standard cell conditioning 1 (CC1) reagent for sample preparation, HER3 monoclonal antibody MAK<humanHER3> M-7.2.42 or HER3 monoclonal antibody MAK<humanHER3> M-7.3.8 as primary antibody and ultraView DAB as detection system.

Figure 4:
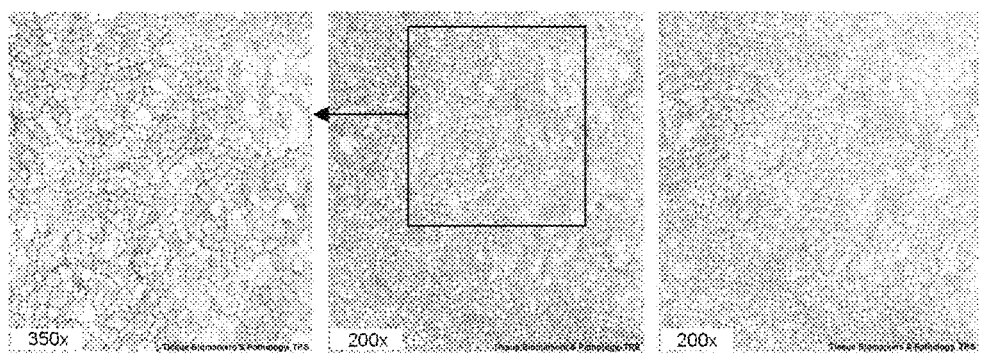

FIG. 4 Comparative immunohistochemistry assays on FFPET Non Small Cell Lung Cancer (NSCLC) samples Comparison of the staining properties and staining patterns of the HER3 monoclonal antibody MAK<humanHER3> M-7.2.42 versus the state of the art anti-HER3 antibody DAK-H3-IC from Dako on routinely formalin fixed paraffin embedded NSCLC tissue.

Left and Middle panels: Immunohistochemistry with HER3 monoclonal antibody MAK<humanHER3> M-7.2.42 on the Ventana Benchmark XT system using the standard cell conditioning 1 (CC1) reagent for sample preparation and ultraView DAB as detection system.

Right panel: Immunohistochemistry with anti-HER3 antibody DAK-H3-IC from Dako on the semi-automated Dako Autostainer platform using the UltraVision LP Detection System and DAB. The procedure of deparaffinization and the antigen retrieval steps were carried out manually. The DAK-H3-IC antibody from Dako cannot be used on the Ventana Benchmark XT system as it does not show any binding activity in FFPET samples on this platform.

Figure 5A:
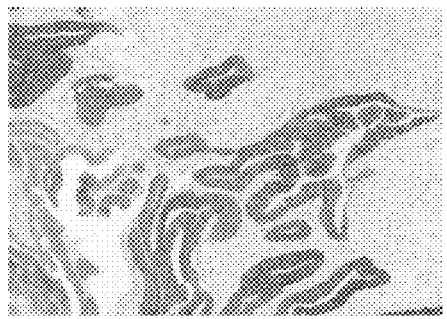
Figure 5A:
Figure 5A:
Figure 5A:

FIG. 5A Comparative immunohistochemistry assays on human tumor tissue samples from colon cancer and lung Comparison of the staining properties and staining patterns of the HER3 monoclonal antibody MAK<humanHER3> M-7.3.8 (left; 0.125 µg/ml) versus the state of the art anti-HER3 antibody C17 from Santa Cruz (right; 0.125 µg/ml) on routinely formalin fixed paraffin tissue samples. In FIG. 5A, the left and right illustrations show binding of MAK<humanHER3> M-7.3.8 and C17, respectively (amplification: 10× (top) and 20× (bottom)) for Human tumor tissue sample Colon A1278-Tp6.

Figure 5B:
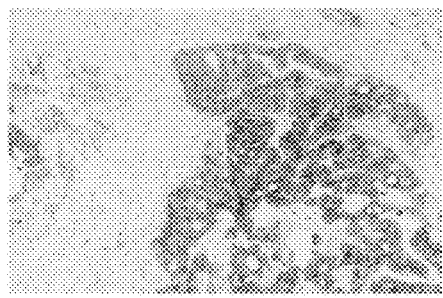
Figure 5B:
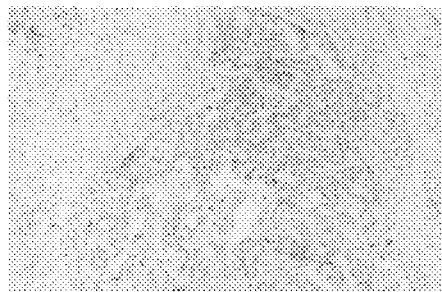
Figure 5B:
Figure 5B:

FIG. 5B Comparative immunohistochemistry assays on human tumor tissue samples from colon cancer and lung Comparison of the staining properties and staining patterns of the HER3 monoclonal antibody MAK<humanHER3> M-7.3.8 (left; 0.125 µg/ml) versus the state of the art anti-HER3 antibody C17 from Santa Cruz (right; 0.125 µg/ml) on routinely formalin fixed paraffin tissue samples. In FIG. 5B, the left and right illustrations show binding of MAK<humanHER3> M-7.3.8 and C17, respectively (amplification: 10× (top) and 20× (bottom)) for Human tumor tissue sample Colon B594 TpS.

Figure 5C:
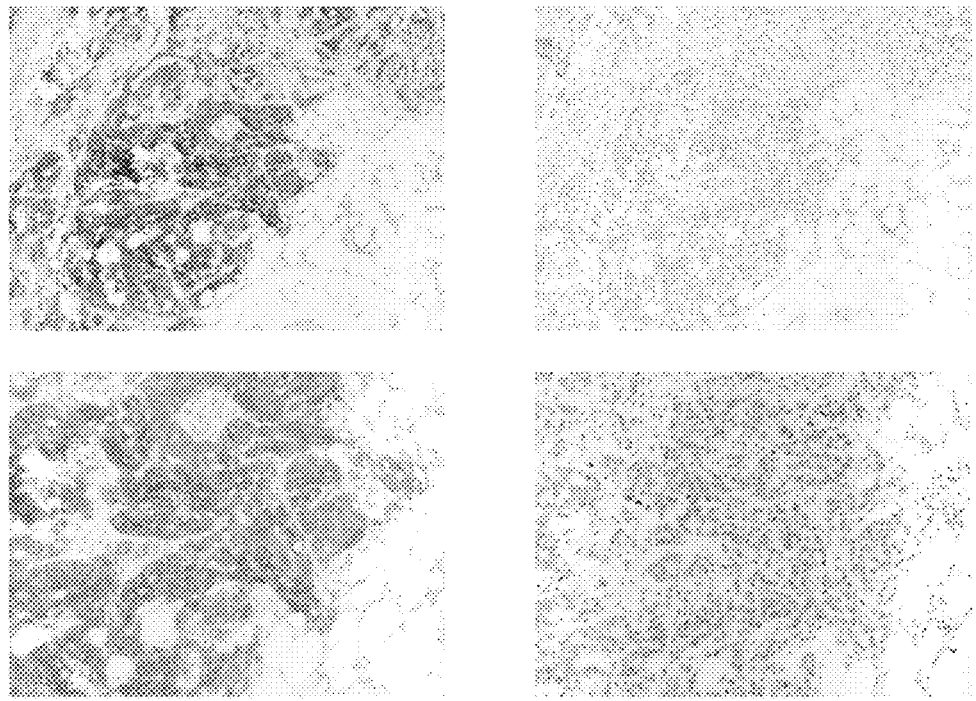

FIG. 5C Comparative immunohistochemistry assays on human tumor tissue samples from colon cancer and lung
Comparison of the staining properties and staining patterns of the HER3 monoclonal antibody MAK<humanHER3> M-7.3.8 (left; 0.125 µg/ml) versus the state of the art anti-HER3 antibody C17 from Santa Cruz (right; 0.125 µg/ml) on routinely formalin fixed paraffin tissue samples. In FIG. 5C, the left and right illustrations show binding of MAK<humanHER3> M-7.3.8 and C17, respectively (amplification: 10× (top) and 20× (bottom)) for Human tumor tissue sample Colon CRC 071147.1.1.

Figure 5D:
Figure 5D:
Figure 5D:
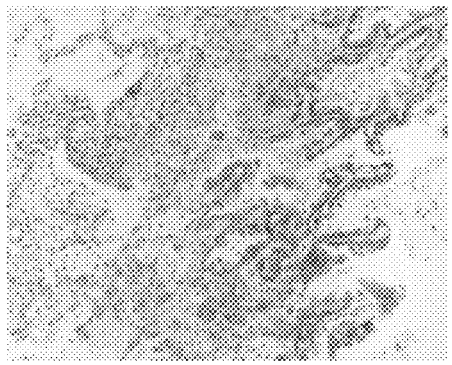
Figure 5D:

FIG. 5D Comparative immunohistochemistry assays on human tumor tissue samples from colon cancer and lung
Comparison of the staining properties and staining patterns of the HER3 monoclonal antibody MAK<humanHER3> M-7.3.8 (left; 0.125 µg/ml) versus the state of the art anti-HER3 antibody C17 from Santa Cruz (right; 0.125 µg/ml) on routinely formalin fixed paraffin tissue samples. In FIG. 5D, the left and right illustrations show binding of MAK<humanHER3> M-7.3.8 and C17, respectively (amplification: 10× (top) and 20× (bottom)) for Human tumor tissue sample Lung p339 Tc16.

DETAILED DESCRIPTION OF THE INVENTION

The present invention relates to an isolated antibody, or an antigen binding portion thereof, which binds to human HER3, characterized in that the heavy chain variable domain comprises a CDR1H region comprising the amino acid sequence of SEQ ID NO: 1, a CDR2H region comprising the amino acid sequence of SEQ ID NO: 2 or SEQ ID NO: 3, and a CDR3H region comprising the amino acid sequence of SEQ ID NO: 4, and the light chain variable domain comprises a CDR1L region comprising the amino acid sequence of SEQ ID NO: 5, a CDR2L region comprising the amino acid sequence of SEQ ID NO: 6 or SEQ ID NO: 7, and a CDR3L region comprising the amino acid sequence of SEQ ID NO: 8.

The present invention further comprises an isolated antibody, or an antigen binding portion thereof, which binds to human HER3, characterized in that the heavy chain variable domain comprises the amino acid sequence of SEQ ID NO: 9 or SEQ ID NO: 10, and the light chain variable domain comprises the amino acid sequence of SEQ ID NO: 11 or SEQ ID NO: 12.

The present invention also comprises an isolated antibody, or an antigen binding portion thereof, which binds to human HER3, characterized in that the heavy chain variable domain comprises a CDR1H region comprising an amino acid sequence modified from SEQ ID NO: 1 by one or more conservative amino acid substitutions at positions, a CDR2H region comprising an amino acid sequence modified from SEQ ID NO: 2 or SEQ ID NO: 3 by one or more conservative amino acid substitutions, and a CDR3H region comprising an amino acid sequence modified from SEQ ID NO: 4 by one or more conservative amino acid substitutions, and a light chain variable domain comprising a CDR1L region comprising an amino acid sequence modified from SEQ ID NO: 5 by one or more conservative amino acid substitutions, a CDR2L region comprising an amino acid sequence modified from SEQ ID NO: 6 or SEQ ID NO: 7 by one or more conservative amino acid substitutions, and a CDR3L region comprising an amino acid sequence modified from SEQ ID NO: 8 by one or more conservative amino acid substitutions.

Another aspect of the present invention provides for an isolated antibody which binds to human HER3, characterized in that the heavy chain variable domain comprises an amino acid sequence with at least 95% sequence identity to SEQ ID NO: 9 or SEQ ID NO: 10, and the light chain variable domain comprises an amino acid sequence with at least 95% sequence identity to SEQ ID NO: 11 or SEQ ID NO: 12.

In one embodiment the antibody according to the present invention is monoclonal.

In another embodiment the antibody of the present invention is an antibody of the IgG subclass.

Unless otherwise explained, all technical and scientific terms used herein have the same meaning as commonly understood by one of ordinary skill in the art to which the invention disclosed herein belongs.

The articles "a" and "an" are used herein to refer to one or to more than one (i.e., to at least one) of the grammatical object of the article. By way of example, "an antibody" means one antibody or more than one antibody.

The term "antibody", as used herein, is intended to refer to immunoglobulin molecules comprised of four polypeptide chains, two heavy (H) chains and two light (L) chains inter-connected by disulfide bands. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion of an antibody" when used herein refers to the amino acid residues of an antibody which are responsible for antigen-binding. The antigen-binding portion of an antibody comprises amino acid residues from the CDRs. The term "antigen-binding portion" of an antibody of the invention contains six CDRs which contribute in varying degrees to the affinity of the binding site for antigen. There are three heavy chain variable domain CDRs (CDR1H, CDR2H and CDR3H) and three light chain variable domain CDRs (CDR1L, CDR2L and CDR3L). The term "CDR1H" denotes the CDR1 region of the heavy chain variable region calculated according to Kabat. CDR2H, CDR3H, CDR1L, CDR2L and CDR3L mean the respective regions from the heavy (H) or light (L) chain. The extent of CDR and FRs is determined by comparison to a compiled database of amino acid sequences in which those regions have been defined according to variability among the sequences according to Kabat et al., Sequences of Proteins of Immunological Interest, 5$^{th}$ Ed. Public Health Service, National Institutes of Health, Bethesda, Md. (1991).

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. An "isolated antibody", as used herein, is also intended to refer to an antibody that is substantially free of other antibodies having different antigenic specificities (e.g., an isolated antibody that specifically binds human HER3 is substantially free of antibodies that specifically bind antigens other than human HER3). An isolated antibody that specifically binds human HER3 may, however, have cross-reactivity to other antigens, such as HER3 molecules from other species. In some embodiments, an antibody is purified to greater than 70% by weight of antibody as determined by, for example, the Lowry method, and in some embodiments, to greater than 80%, 90, 95%, 96%, 97%, 98% or 99% by weight. In one preferred embodiment the isolated antibody according to the present invention is purified to a greater than 90% purity as determined by SDS-PAGE under reducing conditions using Coomassie blue staining for protein detection.

Methods of generating antibodies (such as monoclonal or polyclonal antibodies) are well established in the art (for example, see Harlow and Lane, *Antibodies: A Laboratory Manual*, Cold Spring Harbor Laboratory, New York, 1988). For example peptide fragments of human HER3 can be conjugated to carrier molecules (or nucleic acids encoding such epitopes or conjugated RDPs) can be injected into non-human mammals (such as mice or rabbits), followed by boost injections, to produce an antibody response. Serum isolated from immunized animals may be isolated for the polyclonal antibodies contained therein, or spleens from immunized animals may be used for the production of hybridomas and monoclonal antibodies. In some examples, antibodies are purified before use.

A polyclonal antibody binding to human HER3 can, e.g., be obtained by immunoadsorption using an affinity column containing this sequence as immunosorbent material. In case the isolated antibody is a monoclonal antibody such antibody in some embodiments is purified (1) to greater than 90% antibody as determined by, for example, the Lowry method, and in some embodiments, to greater than 95%, 96%, 97%, 98% or 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain.

In one example, a monoclonal antibody binding to human HER3 can be prepared from murine hybridomas according to the classical method of Köhler and Milstein (*Nature*, 256:495, 1975) or derivative methods thereof. Briefly, a mouse (such as Balb/c) is repetitively inoculated with a few micrograms of a human HER3 peptide fragment or carrier conjugate thereof over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.*, 70:419, 1980), and derivative methods thereof. Selected positive clones can be expanded and their monoclonal antibody product harvested for use.

Whether an antibody binds to human HER3 is easily assessed by an appropriate immunoassay. In one preferred way a peptide of human HER3 is N- or C-terminally labeled with Biotin. One preferred labeling agent is using Fmoc-Glu(biotinyl-PEG)-OH, which incorporates a flexible, hydrophilic spacer between biotin residue and the peptide chain. This biotinylated peptide is bound to a solid phase coated with a biotin binding reagent, e.g., via streptavidin. If an antibody to be analyzed contains a binding site to an epitope within the peptide of human HER3, such antibody binds to the peptide and can be detected by any appropriate means.

The antibody according to the present invention binding to human HER3 preferably has at least a binding affinity of $10^7$ l/mol for this molecule. Also preferred it has an affinity of $10^8$ l/mol or better or of $10^9$ l/mol or better.

As used herein, the terms "binding to human HER3", "specifically binding to human HER3", or "anti-HER3 antibody" are interchangeable and refer to an antibody specifically binding to the human HER3 antigen. As the skilled artisan will appreciate the term "specific" or "specifically binding" is used to indicate that other biomolecules present in the sample do not significantly bind to the antibody that is (specifically) binding to human HER3. The antibody that specifically binds to human HER3 may, however, have cross-reactivity to HER3 molecules from other species. Preferably, the level of binding to a biomolecule other than human HER3 in a sample containing human HER3 results in a binding affinity which is only 10% or less, more preferably only 5% or less of the affinity to human HER3, respectively. The antibody specifically binding to human HER3 will, e.g., not bind human HER2 or other close homologues, i.e., have a binding affinity thereto that is at least 10-fold or preferred at least 20-fold worse as the binding affinity for human HER3

Human HER3 (ErbB-3, ERBB3, c-erbB-3, c-erbB3, receptor tyrosine-protein kinase erbB-3, SEQ ID NO: 17) encodes a member of the epidermal growth factor receptor (EGFR) family of receptor tyrosine kinases which also includes HER1 (also known as EGFR), HER2, and HER4 (Kraus, M. H. et al., PNAS 86 (1989) 9193-9197; Plowman, G. D. et al., PNAS 87 (1990) 4905-4909; Kraus, M. H. et al., PNAS 90 (1993) 2900-2904). The amino acid sequence of human HER3 appears in the amino acid sequence as presently annotated in the UniProtKB/Swiss-Prot database under reference sequence no. P21860. Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase domain (TKD) and a C-terminal phosphorylation domain. This membrane-bound protein has HER3 a Heregulin (HRG) binding domain within the extracellular domain but not an active kinase domain. It therefore can bind this ligand but not convey the signal into the cell through protein phosphorylation. However, it does form heterodimers with other HER family members which do have kinase activity. Heterodimerization leads to the activation of the receptor-mediated signaling pathway and transphosphorylation of its intracellular domain. Dimer formation between HER family members expands the signaling potential of HER3 and is a means not only for signal diversification but also signal amplification. For example the HER2/HER3 heterodimer induces one of the most important mitogenic signals via the PI3K and AKT pathway among HER family members (Sliwkowski M. X., et al., J. Biol. Chem. 269 (1994) 14661-14665; Alimandi M, et al., Oncogene. 10 (1995) 1813-1821; Hellyer, N.J., J. Biol. Chem. 276 (2001) 42153-4261; Singer, E., J. Biol. Chem. 276 (2001) 44266-44274; Schaefer, K. L., Neoplasia 8 (2006) 613-622).

Amplification of this gene and/or overexpression of its protein have been reported in numerous cancers, including prostate, bladder, and breast tumors. Alternate transcriptional splice variants encoding different isoforms have been characterized.

One isoform lacks the intermembrane region and is secreted outside the cell. This form acts to modulate the activity of the membrane-bound form. Additional splice variants have also been reported, but they have not been thoroughly characterized.

An antibody according to the present invention binds to the intracellular region of Her3 and therefore only detects the membrane bound isoform of human HER3 and not the secreted isoform.

As described above, antibodies according to the present invention, i.e., binding to human HER3 can, e.g., be isolated from the serum of an immunized animal by immunoadsorption using a peptide of human HER3.

Monoclonal antibodies can be produced with constant quality and in almost unlimited quantity. In a preferred embodiment the antibody according to the invention is a monoclonal antibody.

Two of the best monoclonal antibodies generated have similar CDRs and surprisingly can be used for a reliable detection of human HER3 in tissue samples, especially in automatic staining systems for FFPET samples.

In one aspect, an anti-HER3 antibody according to the invention comprises a heavy chain variable domain (VH) sequence having at least 90%, 91%, 92%>, 93%>, 94%, 95%, 96%, 97%, 98%, 99%, or 100% sequence identity to the amino acid sequence of SEQ ID NO: 9 or SEQ ID NO: 10. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti HER3 antibody comprising that sequence retains the ability to bind to HER3. In certain embodiments, a total of 1 to 10 amino acids have been substituted, inserted and/or deleted in SEQ ID NO: 9 or in SEQ ID NO: 10. In certain embodiments, substitutions, insertions, or deletions occur in regions outside the CDRs (i.e., in the FRs). Optionally, the anti-HER3 antibody comprises the VH sequence in SEQ ID NO: 9 or in SEQ ID NO: 10, including post-translational modifications of that sequence. In a particular embodiment, the VH comprises one, two or three CDRs selected from: (a) CDR1H comprising the amino acid sequence of SEQ ID NO: 1, (b) CDR2H comprising the amino acid sequence of SEQ ID NO: 2 or SEQ ID NO: 3, and (c) CDR3H comprising the amino acid sequence of SEQ ID NO: 4.

In another aspect, an anti-HER3 antibody according to the invention comprises a light chain variable domain (VL) having at least 90%, 91%, 92%, 93%, 94%, 95%, 96%, 97%, 98%, 99%, or 100% sequence identity to the amino acid sequence of SEQ ID NO: 11 or SEQ ID NO: 12. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HER3 antibody comprising that sequence retains the ability to bind to HER3. In certain embodiments, a total of 1 to 10 amino acids have been substituted, inserted and/or deleted in SEQ ID NO: 11 or in SEQ ID NO: 12. In certain embodiments, the substitutions, insertions, or deletions occur in regions outside the CDRs (i.e., in the FRs). Optionally, the anti-HER3 antibody comprises the VL sequence in SEQ ID NO: 11 or SEQ ID NO: 12, including post-translational modifications of that sequence. In a particular embodiment, the VL comprises one, two or three CDRs selected from (a) CDR1L comprising the amino acid sequence of SEQ ID NO: 5; (b) CDR2L comprising the amino acid sequence of SEQ ID NO: 6 or SEQ ID NO: 7; and (c) CDR3L comprising the amino acid sequence of SEQ ID NO: 8.

In another aspect, an anti-HER3 antibody is provided, wherein the antibody comprises a VH as in any of the embodiments provided above, and a VL as in any of the embodiments provided above. In one embodiment, the antibody comprises the VH and VL sequences in SEQ ID NO: 9 or SEQ ID NO: 10, and SEQ ID NO: 11 or SEQ ID NO: 12, respectively, including post-translational modifications of those sequences.

The term "amino acid" as used within this application denotes the group of naturally occurring carboxy a-amino acids comprising alanine (three letter code: ala, one letter code: A), arginine (arg, R), asparagine (asn, N), aspartic acid (asp, D), cysteine (cys, C), glutamine (gin, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The antibodies according to the invention include, in addition, such antibodies having "conservative sequence modifications" (variant antibodies), nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis or mutation can be introduced by de novo synthetic gene synthesis. As used herein, the terms "conservative amino acid substitution", "conservative substitution", or "conservative sequence modification" are interchangeable and refer to an amino acid substitution, in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-HER3 antibody can be preferably replaced with another amino acid residue from the same side chain family. Exemplary conservative amino acid substitutions are shown in Table 1.

TABLE 1

Exemplary conservative amino acid substitutions

| Original Residue | Very Highly Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

A "variant" anti-HER3 antibody, refers therefore herein to a molecule which differs in amino acid sequence from a "parent" anti-HER3 antibody amino acid sequence by up to ten, preferably from about two to about five, additions, deletions and/or substitutions in one or more variable region of the parent antibody. Amino acid substitutions can be performed by mutagenesis based upon molecular modeling as described by Riechmann, L., et al., Nature 332 (1988) 323-327 and Queen, C, et al., Proc. Natl. Acad. Sci. USA 86 (1989) 10029-10033.

One embodiment of the present invention relates to an isolated antibody, or an antigen binding portion thereof, which binds to HER3, and wherein the CDR1L region comprises an amino acid sequence modified from SEQ ID NO: 5 by a conservative amino acid substitution at position 5. In a further embodiment, the conservative amino acid substitution at position 5 of SEQ ID NO: 5 is a threonine/serin substitution. The term "threoonine/serin substitution" as used herein means that the amino acid threonine in one variant of the anti-HER3 antibody is replaced by serin, or vice versa, serin in one variant of the anti-HER3 antibody is replaced by threonine. The same applies to other specific amino acid substitutions in "variant" anti-HER3 antibodies according to the present invention. For example, in another embodiment of the isolated antibody, or an antigen binding portion thereof, which binds to HER3, the CDR3L region comprises an amino acid sequence modified from SEQ ID NO: 8 by a conservative amino acid substitution at position 6 or position 9, or the CDR3L region comprises an amino acid sequence modified from SEQ ID NO: 8 by a conservative amino acid substitution at position 6 and position 9. In a further embodiment, the conservative amino acid substitution at position 6 of SEQ ID NO: 8 is a valin/alanin substitution or the conservative amino acid substitution at position 9 of SEQ ID NO: 8 is an alanin/threonin substitution. In yet another embodiment, the CDR3L region comprises an amino acid sequence modified from SEQ ID NO: 8 by a conservative amino acid substitution at position 6 and position 9, wherein the conservative amino acid substitution at position 6 of SEQ ID NO: 8 is a valin/alanin substitution and the conservative amino acid substitution at position 9 of SEQ ID NO: 8 is an alanin/threonin substitution.

The antibodies according to the present invention have proven extremely useful in the immunohistochemical detection of human HER3. In one embodiment the present invention relates to a method for performing immunohistochemistry (IHC) the method comprising the steps of a) incubating a tissue sample with an antibody according to the present invention, whereby binding of said antibody to human HER3 in said tissue takes place and b) staining said tissue sample for the anti-HER3 antibody bound in step a).

The term "stain" used as a noun or the term "staining reagent" refers to biological or chemical compounds, and compositions containing such compounds which, when applied to targeted molecules in biological samples, render the molecules detectable (e.g., under microscopic examination). Stains include without limitation detectable nucleic acid probes, antibodies, and other reagents which in combination or by themselves result in a detectable end product. The term "stain" is used interchangeably with the term "dye." The term "stain" used as a verb, or the term "staining," means the contacting of a biological sample with a staining reagent, stain, or dye.

For successful immunostaining of an antigen in a cell or tissue sample at least three criteria have to be met: a) retention of the antigen at its original site, b) accessibility of the antigen and c) correct conformation/preservation of the antigen/epitope of interest.

What is very surprising is the fact that the antibodies according to the present invention also work excellently with tissues samples that had been fixed with formalin and embedded in paraffin.

In one embodiment the present invention relates to an immunohistochemical method for detection of human HER3 with an antibody according to the present invention wherein the tissue sample on which immunostaining is performed is a tissue sample that had been formaldehyde-fixed and paraffin-embedded (FFPE).

Several fixatives are available and used in the routine of a clinical pathology laboratory, like glutardialdehyde, formaldehyde and acetone, or other organic solvents. The vast majority of fixation procedures, however, are based on the use of cross-linking agents, like formaldehyde. The fixative solution usually is an aqueous formaldehyde solution that contains sodium phosphates, contrived to provide buffering (minimal pH change following addition of a small amount of strong acid or base) to pH 7.2-7.6 and an approximately isotonic solution (one whose osmotic pressure is the same as that of mammalian extracellular fluids, often based on physiological saline). The terms formaldehyde and formalin are used interchangeably.

As mentioned before, fixation in formaldehyde is most widely used in clinical pathology. The major reason most likely is that by fixation with formaldehyde the antigen of interest is trapped at the sites it occupied in the living organism. By way of methylene bridges introduced upon formaldehyde fixation also the morphology of a cell or tissue sample is well preserved. These positive effects, however, go to the expense of permeability of the sample and to the fixation causing changes in the accessibility and/or conformation of an antigen/epitope of interest, damage in nucleic acids and inactivation of enzyme activity.

For long term storage a fixed cell or tissue sample usually has to be de-hydrated and embedded in an appropriate embedding medium. Paraffin embedding is usually preferable to either plastic embedding or cutting un-embedded specimens with a vibrating microtome or in a cryostat.

This disclosure provides, among other things, methods for detecting human HER3 in biological samples (e.g., isolated cells or tissues) that have been mounted on a solid surface (e.g., a microscope slide) and treated (e.g., formalin-fixed and paraffin-embedded). One of the advantages of performing immunohistochemistry on FFPE cell or tissue samples is that HER3 in such specimen substantially maintains its position relative to other components, e.g., its location within the cell or tissue sample.

As used herein, the term "detecting" means determining if an agent (e.g., a nucleic acid molecule or protein) or interaction (e.g., binding between an antibody and an antigen, between a protein and a nucleic acid, or between two nucleic acid molecules) is present or absent, for example by making measurements from a sample. In some examples this can further include quantification. In particular examples, an emission signal from a label is detected. Detection can be in bulk, so that a macroscopic number of molecules can be observed simultaneously. Detection can also include identification of signals from single molecules using microscopy and such techniques as total internal reflection to reduce background noise.

For example, use of an antibody specific for a particular protein (e.g., human HER3) permits detection of the protein or protein-protein interaction in a sample, such as an FFPE cell or tissue sample.

The antibody according to the present invention can be detected by direct labeling of the antibody itself, for example, with radioactive labels, fluorescent labels, hapten labels such as, biotin, or an enzyme such as horseradish peroxidase or alkaline phosphatase. Alternatively, unlabeled primary anti-HER3 antibody is used in conjunction with a labeled secondary antibody, comprising antisera, polyclonal antisera or a monoclonal antibody specific for the primary antibody. Immunohistochemistry (IHC) protocols and kits are well known in the art and are commercially available.

Specific binding agents optionally can be directly labeled with a detectable moiety. Useful detection agents include fluorescent compounds (including fluorescein, fluorescein isothiocyanate, rhodamine, 5-dimethylamine-1-napthalenesulfonyl chloride, phycoerythrin, lanthanide phosphors, or the cyanine family of dyes (such as Cy-3 or Cy-5) and the like); bioluminescent compounds (such as luciferase, green fluorescent protein (GFP), or yellow fluorescent protein); enzymes that can produce a detectable reaction product (such as horseradish peroxidase, β-galactosidase, luciferase, alkaline phosphatase, or glucose oxidase and the like), or radiolabels (such as $^3$H, $^{14}$C, $^{15}$N, $^{35}$S, $^{90}$Y, $^{99}$Tc, $^{111}$In, $^{125}$I, or $^{131}$I).

Biological samples useful in a disclosed method are isolated, analyzed in vitro and include any cell preparation or tissue preparation that can be fixed and mounted on a solid surface. Exemplary samples include, without limitation, blood smears, cytocentrifuge preparations, cytology smears, core biopsies, fine-needle aspirates, and/or tissue sections (e.g., cryostat tissue sections and/or paraffin-embedded tissue sections). Exemplary biological samples may be isolated from normal cells or tissues, or from neoplastic cells or tissues. Neoplasia is a biological condition in which one or more cells have undergone characteristic anaplasia with loss of differentiation, increased rate of growth, invasion of surrounding tissue, and which cells may be capable of metastasis. Exemplary neoplastic cells or tissues may be isolated from solid tumors, including breast carcinomas (e.g., lobular and duct carcinomas), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, melanoma, and skin appendage tumors), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage.

A solid support useful in a disclosed method need only bear the biological sample and, optionally, but advantageously, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

Cross-linking due to formaldehyde fixation in general is likely to mask or to destroy epitopes, leading to a false negative immunostaining. It has been found that an epitope on human HER3 as recognized by an antibody according to the present invention can easily be retrieved, e.g., by the standard procedures practiced automatically on the BenchMark analyzer (Ventana Medical Systems, Inc., Tucson, USA). In one embodiment the present invention relates to the use of an antibody as disclosed in the present invention in the detection of HER3 in a formaldehyde-fixed paraffin-embedded tissue (FFPET) sample.

Kits useful for facilitating the practice of an immunohistochemical detection of human HER3 as disclosed herein are also contemplated. In one embodiment, a kit is provided for the detection of human HER3 in a formaldehyde-fixed paraffin-embedded tissue sample, said kit comprising an antibody, or an antigen binding portion thereof, according to the invention, and reagents for the detection of said antibody, or an antigen binding portion thereof.

In particular examples, the antibody, or an antigen binding portion thereof, according to the invention and the reagents for the detection of said antibody, or an antigen binding portion thereof are packaged in separate containers or vials.

In some kit embodiments, the antibody, or an antigen binding portion thereof can be directly labeled, e.g., with a fluorophore, chromophore, or enzyme capable of producing a detectable product (such as alkaline phosphates, horseradish peroxidase and others commonly known in the art).

Other kit embodiments will include secondary detection means; such as secondary antibodies (e.g., goat anti-rabbit antibodies, rabbit anti-mouse antibodies, anti-hapten antibodies) or non-antibody hapten-binding molecules (e.g., avidin or streptavidin). In some such instances, the secondary detection means will be directly labeled with a detectable moiety. In other instances, the secondary (or higher order) antibody will be conjugated to a hapten (such as biotin, DNP, and/or FITC), which is detectable by a detectably labeled cognate hapten binding molecule (e.g., streptavidin (SA) horseradish peroxidase, SA alkaline phosphatase, and/or SA QDot® Nanocrystals™). Some kit embodiments may include colorimetric reagents (e.g., DAB, and/or AEC) in suitable containers to be used in concert with primary or secondary (or higher order) detection means (e.g., antibodies) that are labeled with enzymes for the development of such colorimetric reagents.

In some embodiments, a kit includes positive or negative control samples, such as a cell line or tissue known to express or not express human HER3. In particular examples, control samples are FFPET samples. Exemplary samples include but are not limited to normal (e.g., non-cancerous) cells or tissues.

In some embodiments, a kit includes instructional materials disclosing, for example, means of use of an antibody that specifically binds human HER3. The instructional materials may be written, in an electronic form (e.g., computer diskette or compact disk) or may be visual (e.g., video files). The kits may also include additional components to facilitate the particular application for which the kit is designed. Thus, for example, the kit can include buffers and other reagents routinely used for the practice of an immunohistochemical detection as disclosed herein. Such kits and appropriate contents are well known to those of skill in the art.

Certain kit embodiments can include a carrier means, such as a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes a one or more containers, for instance vials, tubes, and the like that can retain, for example, one or more biological samples to be tested.

Other kit embodiments include, for instance, syringes, cotton swabs, or latex gloves, which may be useful for handling, collecting and/or processing a biological sample. Kits may also optionally contain implements useful for moving a biological sample from one location to another, including, for example, droppers, syringes, and the like. Still other kit embodiments may include disposal means for discarding used or no longer needed items (such as subject samples, etc.). Such disposal means can include, without limitation, containers that are capable of containing leakage from discarded materials, such as plastic, metal or other impermeable bags, boxes or containers.

The terms "nucleic acid" or "nucleic acid molecule", as used herein, are intended to include DNA molecules and RNA molecules. A nucleic acid molecule may be single-stranded or double-stranded, but preferably is double-stranded DNA. A nucleic acid is "operably linked" when it is placed into a functional relationship with another nucleic acid. For example, DNA for a pre-sequence or secretory leader is operable linked to DNA for a polypeptide if it is expressed as a pre-protein that participates in the secretion of the polypeptide; a promoter or enhancer is operable linked to a coding sequence if it affects the transcription of the sequence; or a ribosome binding site is operable linked to a coding sequence if it is positioned so as to facilitate translation. Generally, "operably linked" means that the DNA sequences being linked are co-linear and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice.

One embodiment of the invention is a nucleic acid encoding a heavy and a light chain of an antibody according to the invention.

As used herein, the expressions "cell", "cell line", and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The antibodies according to the invention are preferably produced by recombinant means. Such methods are widely known in the state of the art and comprise protein expression in prokaryotic and eukaryotic cells with subsequent isolation of the antibody polypeptide and usually purification to an acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or *E. coli* cells, and the antibody is recovered from the cells (from the supernatant or after cells lysis). Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880. The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including, column chromatography and others well known in the art (see Ausubel, F., et al., ed. Current Protocols in Molecular Biology, Greene Publishing and Wiley Interscience, New York (1987)). Expression in NS0 cells is described by, e.g., Barnes, L. M., et al, Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al, Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199. Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells. Antibodies obtainable from said cell lines are preferred embodiments of the invention. Afocusylated antibodies are preferably prepared via glycoengineering as described above.

Amino acid sequence variants of anti-HER3 antibody are prepared by introducing appropriate nucleotide changes into the antibody encoding DNA, or by peptide synthesis. Such modifications can be performed, however, only in a very limited range, e.g., as described above. For example, the modifications do not alter the abovementioned antibody characteristics such as the IgG isotype and epitope binding, but may improve the yield of the recombinant production, protein stability, or facilitate the purification. Any cysteine residue not involved in maintaining the proper conformation of the anti-HER3, antibody may also be substituted, generally with serine, to improve the oxidative stability of the molecule and to prevent aberrant crosslinking. Conversely, cysteine bond(s) may be added to the antibody to improve its stability (particularly where the antibody is an antibody fragment such as an Fv fragment). Another type of amino acid variant of the antibody alters the original glycosylation pattern of the antibody. By "altering" is meant removing one or more carbohydrate moieties found in the antibody and/or adding one or more glycosylation sites that are not present in the antibody.

Glycosylation of antibodies is typically N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Nucleic acid molecules encoding amino acid sequence variants of anti-HER3 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-HER3 antibody.

Another type of covalent modification of the antibody comprises linking the antibody to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670, 417; 4,791,192; 4,179,337.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

The following sequence listing, examples and figures are provided to aid the understanding of the present invention, the true scope of which is set forth in the appended claims. It is understood that modifications can be made in the procedures set forth without departing from the spirit of the invention.

Example 1

Generation of Monoclonal Antibodies to HER3

For the generation of a monoclonal antibody eight week old female Balb/c mice were immunized intraperitoneally with 100 µg of a HER3 antigen peptide emulsified in cFA. The antigen previously was synthesized employing an automated peptide synthesizer, equipped with a suitable spacer and coupled N-terminally to KLH (Keyhole Limphet Hemocyanine). The initial immunization was followed by three further immunizations with iFA after 6 weeks at monthly intervals. Three days before spleen removal mice were boosted intravenously with 50 µg of the antigen. Spleen cells and P3X63Ag8.653 myeloma cells were fused with PEG and cultured in HAz selection medium. After removal, single cell preparations of the spleen were made and spleen cells were fused to myeloma cells as e.g. described in Köhler and Milstein (1975). Resulting hybridomas were screened with ELISA for reactivity against a biotinylated screening peptide with a sequence corresponding to the used immunogen. Streptavidin coated 384-well MTPs were coated with biotinylated HER3 peptide and incubated with undiluted hybridoma supernatants. Plates were then probed with HRP-labeled sheep anti-murine IgG-Fc specific antibody and developed with ABTS. The binding affinity of the selected hybridomas was tested by Biacore analysis. Hybridomas with high affinity for their respective immunogen sequence were cloned by single cell deposition using a FACSAria III. The resulting monoclonal subclones were again tested by ELISA and Biacore analysis.

Example 2

Testing of Hybridoma Culture Supernatants by Biacore-Analysis

For selection of suitable antibodies, a kinetic screening was performed on hybridoma culture supernatants. The measurements were done using Biacore SPR technology. The CM5 series S sensor chip was mounted into an A100 instrument (GE Healthcare, Biacore) and was hydrodynamically addressed in HBSN buffer (10 mM HEPES pH 7.4, 150 mM NaCl) according to the manufacturer's instructions. The system buffer was HBS-ET (10 mM HEPES pH 7.4, 150 mM NaCl, 0.05% TWEEN 20). The sample buffer was the system buffer supplemented with 1 mg/ml CMD (Carboxymethyldextrane, Sigma #86524). The system was driven at 25° C.

10000 RU RAMIgGFC (relative units of rabbit-anti-mouse F(c)gamma-fragment of the respective mouse immunoglobulin G subclass/Jackson Laboratories) were immobilized according to the manufacturer's instructions using EDC/NHS chemistry on the flow cells FC1 (anti-mouse F(c)gamma of subclass 1), FC2, FC3 and FC4, respectively, on the sensitive spots 1, 2, 4 and 5 on each flow cell. The spots were deactivated using 1M ethanolamine.

The binding activity of antibodies against the HER3 peptide was kinetically tested. Antibodies were captured by a 1 min injection at 10 µl/min of crude hybridoma supernatants diluted 1:3 in sample buffer. Biotinylated Her-3 peptides were carefully singly grafted on streptavidin to enlarge the molecular weight of the complexes and to increase the mass sensitivity of the system. Since the antigen complex dissociation $k_d$ is independent of the analyte injection concentration, this is a legal method to increase the sensitivity of the system.

The respective peptide-graft was injected for 5 min at 30 µl/min and dissociation was monitored for 3 min. Acidic regeneration of the sensor surface using 3 consecutive injections of 10 mM Glycine pH 1.5 at 30 µl/min.

Data was evaluated using the Biaevaluation A100 software V.1.1 according to the manufacturer's instructions. Binding Late (RU), Stability Late (RU), $R_{Max}$, $k_d$ (1/s) and MR (Molar Ratio) were calculated. Clones were scored according to their antigen complex stability and MR.

Data was evaluated using the Biaevaluation software V.4.1 according to the manufacturer's instructions. The dissociation rate constants $k_d$ (1/s) were calculated and t1/2 diss was calculated t1/2diss=ln(2)/60*kd [min]. The respective data are shown in Table 2.

TABLE 2

Kinetic parameters of anti-HER3 monoclonal antibody clones

| monoclonal antibody | Isotype | kd [1/s] | t½ diss [min] |
|---|---|---|---|
| MAK < humanHER3 > M-1.1.1 | IgG1K | 4.26E−04 | 27 |
| MAK < humanHER3 > M-1.2.2 | IgG1K | 4.18E−04 | 28 |
| MAK < humanHER3 > M-1.1.4 | IgG2aK | 2.92E−04 | 40 |
| MAK < humanHER3 > M-6.3.1 | IgG1K | 9.28E−04 | 12 |
| MAK < humanHER3 > M- 7.3.8 | IgG2aK | 2.66E−05 | 435 |
| MAK < humanHER3 > M- 7.2.42 | IgG2aK | 4.26E−05 | 271 |

Monoclonal antibodies MAK<humanHER3> M-7.3.8 and MAK<humanHER3> M-7.2.42 show a complex stability t1/2 diss sufficient for an application on the Ventana Benchmark XT platform.

Especially the rather slow dissociation is of critical importance for IHC-staining using the automated Ventana Benchmark XT platform.

As obvious from Table 2 a very slow dissociation is observed with the monoclonal antibodies produced by hybridoma (clones) MAK<humanHER3> M-7.3.8 and MAK<humanHER3> M-7.2.42, with MAK<humanHER3> M-7.3.8 showing the slowest dissociation.

Example 3

Western Blotting

Comparative Western Blotting analysis was performed using the newly generated HER3 monoclonal antibodies MAK<humanHER3> M-7.2.42, MAK<humanHER3> M-7.3.8 and the monoclonal antibody DAK-H3-IC from Dako.

a) Comparative Western Blot Assays with Several Transfected Control Cell Lines

Lysates were prepared from several HEK293 control cell lines. The cells were transiently transfected with plasmids coding for HER1, HER2, HER3 or HER4. HEK293 cells transfected with the mammalian expression vector pRK5 were used as negative control. For western blotting 10 µg protein lysates were loaded per lane on 4-12% NuPage SDS gels (Invitrogen). Western blotting was performed according to standard protocols with standard NuPage buffers and reagents (Invitrogen). After blocking the membrane was incubated with MAK<humanHER3> M-7.2.42, MAK<humanHER3> M-7.3.8 or the HER3 monoclonal antibody DAK-H3-IC from Dako. MAK<humanHER3> M-7.2.42 and MAK<humanHER3> M-7.3.8 were used at a concentration of 1ng/ml. Primary antibody incubation was performed for 60 min at RT and at 37° C. HRP-conjugated anti-mouse Fab was used as secondary antibody. The dilution of DAK-H3-IC antibody was made as recommended by its manufacturer and the choice of secondary (detection) antibody was adapted as required. The membrane was developed with ECL (Amersham) and exposed to an x-ray film.

Figure 1:
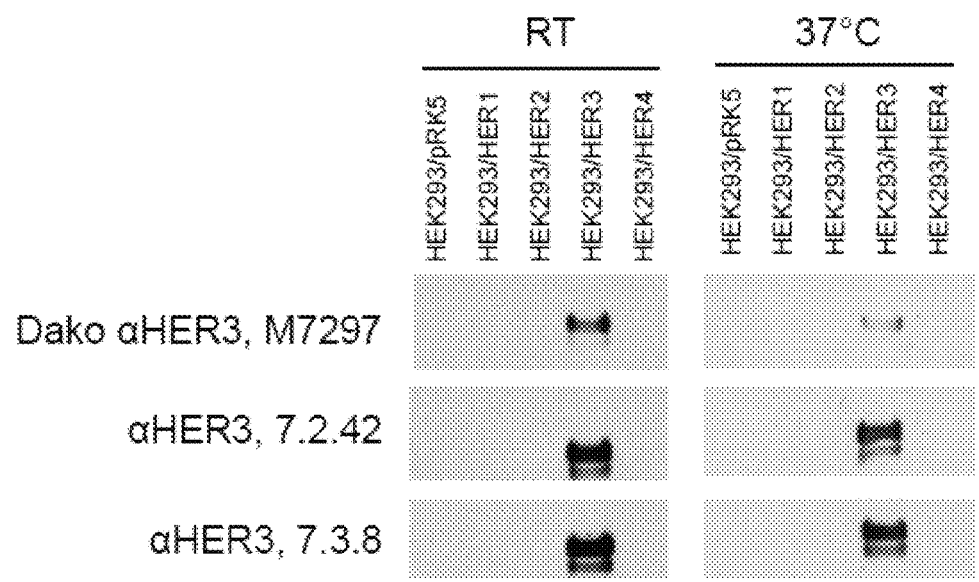
FIG. 1 Comparative Western Blot assays with several transfected control cell lines Cell lysates prepared from transfected HEK293 cell lines overexpressing HER1, HER2, HER3, HER4, or transfected with the mammalian expression vector pRK5 (as negative control) were separated by SDS-PAGE and transferred to a nitrocellulose membrane. After blocking the membrane was incubated with HER3 monoclonal antibody MAK<humanHER3> M-7.2.42 or with HER3 monoclonal antibody MAK<humanHER3> M-7.3.8 or the monoclonal state of the art anti-HER3 antibody DAK-H3-IC from Dako at RT or 37° C. HRP-conjugated anti-mouse Fab was used as secondary antibody.

Results of the individual blots are given in FIG. 1. The comparative Western Blot analysis indicates that the newly developed MAK<humanHER3> M-7.2.42 and MAK<humanHER3> M-7.3.8 specifically detect HER3 and show no cross reactions with HER1, HER2, HER4 or other proteins. These binding characteristics can be found at RT and 37° C., whereas the HER3 monoclonal antibody DAK-H3-IC from Dako shows a significant weaker binding activity at 37° C. As such, the newly developed MAK<humanHER3> M-7.2.42 and MAK<humanHER3> M-7.3.8 show superior binding characteristics in Western Blot assays in comparison to the state of the art monoclonal anti-HER3 antibody DAK-H3-IC from Dako, particularly under temperature conditions as used in automated staining systems.

b) Comparative Western Blot Assays with Non Small Cell Lung Cancer (NSCLC) Samples Fresh frozen NSCLC samples with different HER3 expression levels from 0 to high of were lysed and analyzed with MAK<humanHER3> M-7.2.42 or the antibody DAK-H3-IC from Dako at 37° C. analogous to the SDS-PAGE/Western blotting procedure described in Example 3a).

Figure 2:
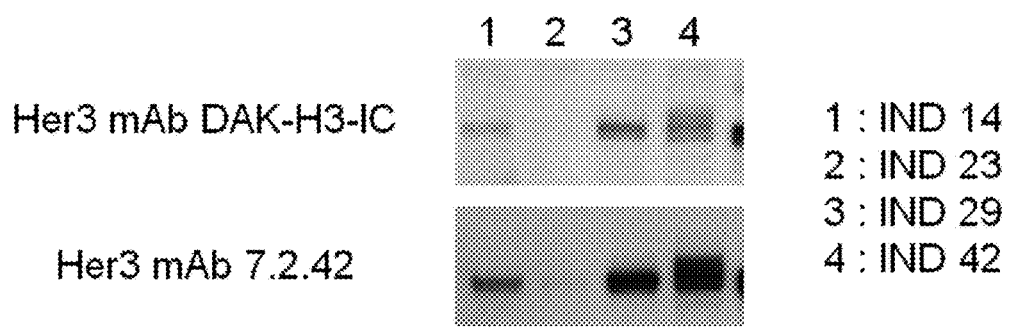
FIG. 2 Comparative Western Blot assays with Non Small Cell Lung Cancer (NSCLC) samples Cell lysates prepared from fresh frozen NSCLC samples were separated by SDS-PAGE and transferred to a nitrocellulose membrane. After blocking the membrane was incubated with HER3 monoclonal antibody MAK<humanHER3>M-7.2.42 or the monoclonal state of the art anti-HER3 antibody DAK-H3-IC from Dako at 37° C. HRP-conjugated anti-mouse Fab was used as secondary antibody.

Results of the individual blots are given in FIG. 2. The comparative Western Blot analysis indicates that the newly developed MAK<humanHER3> M-7.2.42 shows significantly higher binding sensitivity towards HER3 in comparison to the state of the art monoclonal anti-HER3 antibody DAK-H3-IC from Dako.

Example 4

Sequencing

To obtain the DNA sequences of the selected hybridoma clones a 5' Race PCR was conducted. For the RT-PCR total RNA was prepared from $5 \times 10^6$ cells by using a total RNA purification kit (Qiagen). The reverse transcription and the PCR were conducted using a 5'prime RACE PCR kit (Roche). The resulting PCR fragments from heavy and light chain were purified by gel electrophoresis with subsequent gel extraction. The PCR fragments were cloned using the Topo Zero-Blunt cloning kit (Invitrogen) and transformed into chemically competent cells. Several clones from each hybridoma were submitted for sequencing to obtain a consensus sequences for the selected clones.

Example 5

Immunohistochemistry a) Immunohistochemistry on Cell Line Control Samples Using the Monoclonal Antibody MAK<humanHER3> M-7.2.42 and MAK<humanHER3> M-7.3.8

The suitability of the newly developed HER3 monoclonal antibodies MAK<humanHER3> M-7.2.42 and MAK<humanHER3> M-7.3.8 was shown using FFPE cell line controls. Therefore HER1, HER2, HER3 or HER4 transfected or untransfected HEK293 cells, respectively, were fixed with 4% PBS buffered formaldehyde and were subsequently embedded in paraffin.

All staining procedures were performed on the Ventana Benchmark XT automated IHC stainer using Ventana buffers and reagents, i.e., amongst others, the standard cell conditioning 1 (CC1) reagent for sample preparation and ultraView DAB as detection system.

Figure 3:
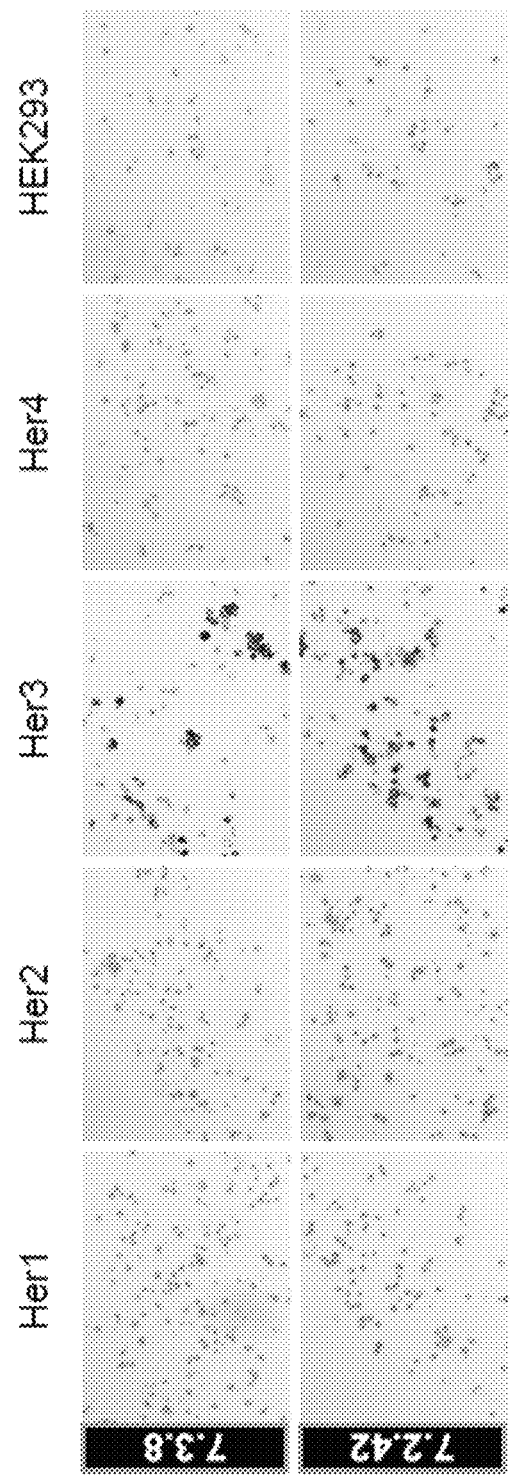
FIG. 3 Immunohistochemistry on cell line control samples using the monoclonal antibodies MAK<humanHER3> M-7.2.42 and MAK<humanHER3> M-7.3.8

As obvious from FIG. 3 the newly developed HER3 monoclonal antibodies MAK<humanHER3> M-7.2.42 and MAK<humanHER3> M-7.3.8 show specific membrane staining only on HER3 transfected cells. HER1, HER2 and HER4-transfected cells and control cells are negative. HER3 monoclonal antibodies MAK<humanHER3> M-7.2.42 and MAK<humanHER3> M-7.3.8 show good IHC-staining with HER3 transfected cells if used according to standard protocols on the Ventana Benchmark XT analyzer (see FIG. 3, HER3 captioned cell staining).

b) Comparative Immunohistochemistry Assays on FFPET Non Small Cell Lung Cancer (NSCLC) Samples The monoclonal antibody MAK<humanHER3> M-7.2.42 was further evaluated for suitability of immunohistochemistry staining from formalin-fixed paraffin-embedded tissue (FFPET) samples in comparison to the monoclonal state of the art antibody DAK-H3-IC from Dako. The immunohistochemistry assays were performed on routinely formalin fixed paraffin embedded NSCLC tissue samples. The staining with MAK<humanHER3> M-7.2.42 was performed on the Ventana Benchmark XT platform using standard reagents and procedures, i.e., amongst others, the standard cell conditioning 1 (CC1) reagent for sample preparation and ultraView DAB as detection system. The immunohistochemistry assay with Dako's DAK-H3-IC antibody against HER3 was performed on the semi-automated Dako Autostainer platform using the UltraVision LP Detection System and DAB. The procedure of deparaffinization and the antigen retrieval steps were carried out manually. The DAK-H3-IC antibody from Dako cannot be used on the Ventana Benchmark XT system as it does not show any binding activity in FFPET samples on this platform.

As obvious from FIG. 4A, which is an enlarged section of the tissue sample shown in FIG. 4B, the newly developed monoclonal antibody MAK<humanHER3> M-7.2.42 shows strong membrane staining on tumor cells. The staining intensity is significantly stronger than the staining intensity obtained with Dako's DAK-H3-IC state of the art antibody against HER3. As such, monoclonal antibody MAK<humanHER3> M-7.2.42 shows high binding specificity and sensitivity towards HER3 in FFPET samples and provides for a reliable detection of HER3 expression when used in automated systems for staining clinical human tumor samples.

c) Comparative Immunohistochemistry Assays on Human Tumor Tissue Samples from Colon Cancer and Lung To analyze the sensitivity of new anti-Her3 antibodies for immunohistochemistry as compared to commercially available antibodies, stainings of consecutive sections were performed. 3 μm consecutive sections from formalin fixed paraffin embedded human tumor tissues from lung and colon cancer were prepared. All stainings were performed on the Roche/Ventana Benchmark XT instrument. For antigen retrieval buffer CC1 was applied for 60 min, followed by staining with the different primary antibodies (MAK<humanHER3> M-7.3.8 and Santa Cruz C17). Primary antibody detection was done using the Ventana OptiView Kit. Both antibodies were used at a concentration of 125 ng/ml.

As shown in FIGS. 5A to D antibody MAK<humanHER3> M-7.3.8 can clearly detect the expression and membrane localization of Her3 within tumor tissues, even when Her3 is expressed in low amounts. Compared to the new antibody 7.3.8 the staining of the same tumor cases with the commercial antibody C17 was not detectable.

The invention claimed is:

1. An isolated antibody, or an antigen binding portion thereof, which binds to human HER3, wherein
the heavy chain variable domain comprises
a CDR1H region comprising the amino acid sequence of SEQ ID NO: 1,
a CDR2H region comprising an amino acid sequence selected from the group consisting of SEQ ID NO: 2 and SEQ ID NO: 3,
and a CDR3H region comprising the amino acid sequence of SEQ ID NO: 4,
and the light chain variable domain comprises
a CDR1L region comprising the amino acid sequence of SEQ ID NO: 5,
a CDR2L region comprising the amino acid sequence selected from the group consisting of SEQ ID NO: 6 and SEQ ID NO: 7,
and a CDR3L region comprising the amino acid sequence of SEQ ID NO: 8.

2. The antibody, or an antigen binding portion thereof, according to claim 1, wherein
the heavy chain variable domain comprises the amino acid sequence selected from the group consisting of SEQ ID NO: 9 and SEQ ID NO: 10, and the light chain variable domain comprises the amino acid sequence selected from the group consisting of SEQ ID NO: 11 and SEQ ID NO: 12.

3. An isolated antibody, or an antigen binding portion thereof, which binds to human HER3, wherein
the heavy chain variable domain comprises
a CDR1H region comprising the amino acid sequence of SEQ ID NO: 1,
a CDR2H region comprising the amino acid sequence of SEQ ID NO: 2 or SEQ ID NO: 3,
and a CDR3H region comprising the amino acid sequence of SEQ ID NO: 4,
and the light chain variable domain comprises
a CDR1L region comprising the amino acid sequence of SEQ ID NO: 5 modified by a conservative amino acid substitution, wherein the conservative amino acid substitution is a threonine/serine substitution at position 5 of SEQ ID NO: 5,
a CDR2L region comprising the amino acid sequence of SEQ ID NO: 6 or SEQ ID NO: 7,
and a CDR3L region comprising the amino acid sequence of SEQ ID NO: 8.

4. The antibody, or an antigen binding portion thereof, according to claim 1, wherein the antibody is a monoclonal antibody.

5. A method for performing immunohistochemistry the method comprising the steps of
a) incubating a tissue sample with an antibody, or an antigen binding portion thereof, according to claim 1, whereby binding of said antibody to HER3 in said tissue takes place and
b) staining said tissue sample for the anti-HER3 antibody bound in step (a).

6. The method according to claim 5, wherein said tissue sample is a tissue sample that had been formaldehyde-fixed and paraffin-embedded (FFPE).

7. The method according to claim 5, wherein steps a) and b) are performed using an automated instrument.

8. A kit for the detection of human HER3 in a formaldehyde-fixed paraffin-embedded tissue (FFPET) sample, said kit comprising:
an antibody, or an antigen binding portion thereof, according to claim 1; and
reagents for the detection of said antibody, or an antigen binding portion thereof.

9. A nucleic acid encoding a heavy and light chain of an antibody binding to human HER3, wherein the antibody comprises a heavy chain variable domain and a light chain variable domain according to claim 1.

10. An isolated antibody, or an antigen binding portion thereof, which binds to human HER3, wherein
the heavy chain variable domain comprises
a CDR1H region comprising the amino acid sequence of SEQ ID NO: 1,
a CDR2H region comprising an amino acid sequence selected from the group consisting of SEQ ID NO: 2 and SEQ ID NO: 3,
and a CDR3H region comprising the amino acid sequence of SEQ ID NO: 4,
and the light chain variable domain comprises a CDR1L region comprising the amino acid sequence of SEQ ID NO: 5,
a CDR2L region comprising an amino acid sequence selected from the group consisting of SEQ ID NO: 6 and SEQ ID NO: 7, and a CDR3L region comprising an amino acid sequence modified from SEQ ID NO: 8 by one or two conservative amino acid substitutions, wherein the one or two conservative amino acid substitutions is/are a valine/alanine substitution at position 6 of SEQ ID NO: 8 and/or an alanine/threonine substitution at position 9 of SEQ ID NO: 8.

11. The antibody, or an antigen binding portion thereof, according to claim 3, wherein the antibody is a monoclonal antibody.

12. A method for performing immunohistochemistry the method comprising the steps of
   a) incubating a tissue sample with an antibody, or an antigen binding portion thereof, according to claim 3, whereby binding of said antibody to HER3 in said tissue takes place and
   b) staining said tissue sample for the anti-HER3 antibody bound in step (a).

13. The method according to claim 12, wherein said tissue sample is a tissue sample that had been formaldehyde-fixed and paraffin-embedded (FFPE).

14. The method according to claim 12, wherein steps a) and b) are performed using an automated instrument.

15. A kit for the detection of human HER3 in a formaldehyde-fixed paraffin-embedded tissue (FFPET) sample, said kit comprising:
   an antibody, or an antigen binding portion thereof, according to claim 3; and
   reagents for the detection of said antibody, or an antigen binding portion thereof.

16. The antibody, or an antigen binding portion thereof, according to claim 10, wherein the antibody is a monoclonal antibody.

17. A method for performing immunohistochemistry the method comprising the steps of
   a) incubating a tissue sample with an antibody, or an antigen binding portion thereof, according to claim 10, whereby binding of said antibody to HER3 in said tissue takes place and
   b) staining said tissue sample for the anti-HER3 antibody bound in step (a).

18. The method according to claim 17, wherein said tissue sample is a tissue sample that had been formaldehyde-fixed and paraffin-embedded (FFPE).

19. The method according to claim 17, wherein steps a) and b) are performed using an automated instrument.

20. A kit for the detection of human HER3 in a formaldehyde-fixed paraffin-embedded tissue (FFPET) sample, said kit comprising:
   an antibody, or an antigen binding portion thereof, according to claim 10; and
   reagents for the detection of said antibody, or an antigen binding portion thereof.

* * * * *